(12) United States Patent
McCaffrey et al.

(10) Patent No.: US 10,117,565 B2
(45) Date of Patent: Nov. 6, 2018

(54) METHODS AND APPARATUS FOR CALIBRATION OF A SENSOR ASSOCIATED WITH AN ENDOSCOPE

(71) Applicant: Boston Scientific Scimed, Inc., Maple Grove, MN (US)

(72) Inventors: Nathaniel McCaffrey, Hampton Falls, NH (US); Jane Bareau, Needham, MA (US); Laura Keith, Acton, MA (US); James McNally, San Diego, CA (US); Jason Sproul, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/641,019

(22) Filed: Jul. 3, 2017

(65) Prior Publication Data

US 2017/0296041 A1  Oct. 19, 2017

Related U.S. Application Data

(63) Continuation of application No. 14/196,897, filed on Mar. 4, 2014, now Pat. No. 9,723,972.

(60) Provisional application No. 61/772,373, filed on Mar. 4, 2013.

(51) Int. Cl.
*A61B 1/00* (2006.01)

(52) U.S. Cl.
CPC ...... *A61B 1/00131* (2013.01); *A61B 1/00057* (2013.01)

(58) Field of Classification Search
CPC ............ A61B 1/00057; A61B 1/00059; A61B 1/00131
USPC .......... 250/205, 221; 382/128; 600/109, 117
See application file for complete search history.

(56) References Cited

U.S. PATENT DOCUMENTS

| 6,734,958 | B1 | 5/2004 | MacKinnon et al. |
|---|---|---|---|
| 7,699,477 | B2 | 4/2010 | Hirata |
| 9,544,582 | B2 * | 1/2017 | Kummailil ........... H04N 17/002 |
| 9,723,972 | B2 * | 8/2017 | McCaffrey ......... A61B 1/00057 |
| 2001/0051761 | A1 | 12/2001 | Khadem |
| 2003/0007672 | A1 | 1/2003 | Harman et al. |
| 2008/0097156 | A1 | 4/2008 | Nakamura |
| 2009/0139300 | A1 | 6/2009 | Pugh et al. |
| 2010/0060658 | A1 | 3/2010 | Fujii et al. |
| 2012/0268579 | A1 | 10/2012 | Zhao et al. |
| 2014/0142383 | A1 | 5/2014 | Blumenzweig et al. |

* cited by examiner

*Primary Examiner* — Kevin Pyo
(74) *Attorney, Agent, or Firm* — Bookoff McAndrews, PLLC

(57) ABSTRACT

Embodiments of the invention include an apparatus including an enclosure configured to receive an endoscope having an electromagnetic radiation sensor. The apparatus also includes an electromagnetic radiation source having at least a portion disposed within the enclosure. The electromagnetic radiation source is configured to emit electromagnetic radiation based on a calibration instruction. The electromagnetic radiation sensor is configured to receive at least a portion of the electromagnetic radiation when at least a portion of the endoscope is coupled to the enclosure.

20 Claims, 10 Drawing Sheets

METHODS AND APPARATUS FOR CALIBRATION OF A SENSOR ASSOCIATED WITH AN ENDOSCOPE

CROSS-REFERENCE TO RELATED APPLICATIONS

This application is a continuation of U.S. application Ser. No. 14/196,897, filed Mar. 4, 2014, which claims the benefit of priority from U.S. Provisional Application No. 61/772,373, filed on Mar. 4, 2013, each of which is incorporated by reference herein in its entirety.

FIELD

Embodiments of the invention relate generally to calibration of an endoscope, and, in particular, to methods and apparatus for calibration of a sensor associated with an endoscope.

BACKGROUND

An image detector in one endoscope can have a responsiveness that is different than the responsiveness of an image detector in another endoscope, even if the image detectors are similarly configured and were produced using the same process. Even a single image detector of an endoscope can have individual pixels that respond differently to incident light relative to other pixels of that image detector. Often, the variations in responsiveness can be caused by, for example, different operating conditions and/or manufacturing variations (e.g., semiconductor processing variation). Furthermore, the responsiveness of an image detector of an endoscope can change as the image detector and/or endoscope ages. Variations in the responsiveness of image detectors can be undesirable in many endoscopic applications (e.g., clinical applications).

Known calibration procedures can be used to equalize and normalize the responsiveness of image detectors of endoscopes (e.g., pixel-to-pixel, endoscope-to-endoscope). These calibration procedures, however, can be performed using a disposable endoscope cover that cannot be used more than once. In addition, these disposable endoscope covers can be limited to a single target pattern. Alternatively, the calibration procedures can be performed using a reusable calibration cup (or cover) that can degrade with age and when not cleaned properly. In addition, the cup can be limited to use with a uniform white field with no target pattern. Thus, a need exists for a multi-use endoscopic calibration unit that can have multiple targets and related methods.

SUMMARY

In one embodiment, an apparatus includes an enclosure configured to receive an endoscope having an electromagnetic radiation sensor. The apparatus also includes an electromagnetic radiation source having at least a portion disposed within the enclosure. The electromagnetic radiation source is configured to emit electromagnetic radiation based on a calibration instruction. The electromagnetic radiation sensor is configured to receive at least a portion of the electromagnetic radiation when at least a portion of the endoscope is coupled to the enclosure.

In another embodiment, a method includes emitting electromagnetic radiation at a first time from an electromagnetic radiation source that has at least a portion disposed within an enclosure. The method also includes receiving a signal from a sensor, and the signal is defined based on a portion of the electromagnetic radiation received at the sensor while at least a portion of an endoscope is received within the enclosure. The method further includes emitting electromagnetic radiation at a second time different than the first time in response to the signal and based on a calibration algorithm associated with the endoscope.

In a further embodiment, an apparatus includes an adapter including an opening configured to be coupled to a portion of an endoscope. The apparatus also includes a calibration unit including a calibration target disposed within the calibration unit. The calibration unit is configured to receive the adapter such that an image sensor of the endoscope has a specified position relative to the calibration target when the adapter is coupled to the calibration unit and the endoscope is coupled to the adapter.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
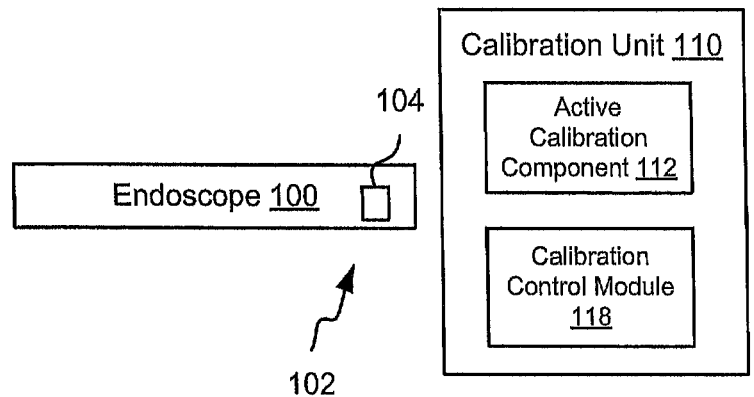
FIG. 1 is a schematic diagram that illustrates an endoscope, and a calibration unit configured to receive the endoscope and calibrate a sensor associated with the endoscope, according to an embodiment of the invention.

Reference will now be made in detail to exemplary embodiments, examples of which are illustrated in the accompanying drawings. Wherever possible, the same reference numbers and terminology will be used throughout the drawings to refer to the same or like parts. Any aspect set forth in any embodiment may be used with any other embodiment set forth herein.

In one embodiment, a calibration unit can be configured to receive at least a portion of an endoscope such that one or more sensors associated with the endoscope can be calibrated using a calibration target at least partially disposed within an enclosure defined by the calibration unit. A sensor associated with the endoscope can be referred to as an endoscopic sensor. An endoscopic sensor can be, for example, an electromagnetic (EM) radiation sensor coupled to the endoscope (e.g., disposed within or on) and configured to function as an image detector. Such an image detector can be configured to receive and convert EM radiation reflected from an object into one or more image-detector signals that can be used to produce one or more images of the object on a display. The EM radiation can include, for example, radio waves, microwaves, terahertz radiation, infrared radiation, visible light, ultraviolet radiation, x-rays, gamma rays, and/or so forth.

The calibration unit can be configured to calibrate an endoscopic sensor based on a calibration instruction(s) (e.g., set of calibration instructions, calibration algorithm) associated with (e.g., defining) a calibration procedure. The calibration procedure can have, for example, a pre-calibration portion, a calibration portion, and/or a calibration test portion (which can be part of, for example, a post-calibration portion). The calibration unit can be configured to calibrate an endoscopic sensor based on a signal(s) (e.g., feedback signal, control signal) associated with one or more components of the calibration unit. The calibration unit can also be in communication with the endoscope and can be configured to calibrate the endoscopic sensor based on a signal(s) (e.g., feedback signal, control signal) associated with one or more components of the endoscope (e.g., processor, endoscopic sensor).

In some embodiments, the calibration unit can have an active calibration component that can be configured to define a calibration target (e.g., a position, an image) for various calibration procedures and/or the calibration of a variety of endoscopes (e.g., endoscopic sensors). For example, the active calibration component can be configured to define a calibration target in response to a calibration instruction associated with a calibration procedure associated with a particular endoscope. In some embodiments, the calibration unit can be configured to, for example, detect an endoscope (and/or endoscopic sensor) type/characteristic and trigger execution of a calibration instruction accordingly.

The active calibration component can include, for example, an EM radiation source configured to emit EM radiation defining a calibration target. The EM radiation source can be configured to emit EM radiation, for example, at specified times (e.g., during pre-calibration, during calibration, during post-calibration test) and/or in a specified arrangement. In some embodiments, the active calibration component can include one or more actuators configured to move, for example, a portion of the active calibration component (e.g., EM radiation source) to a specified position within the calibration unit.

In some embodiments, the calibration unit can be configured to receive an adapter(s) that is configured to receive a portion of an endoscope(s) such that an endoscopic sensor has, for example, a specified position (e.g., distance, rotational orientation) relative to a component (e.g., calibration target, photodetector) associated with the calibration unit. In some embodiments, a calibration unit can include one or more components (e.g., sensor, detector, processor) configured to determine whether or not a portion of an endoscope and/or an adapter has been received in a desirable manner by the calibration unit before calibration of a sensor associated with the endoscope. In some embodiments, the calibration unit and/or the adapter can have one or more removable components. In some embodiments, the calibration unit, the adapter, and/or the endoscope can have a variety of shapes with any combination of curved and straight portions.

FIG. 1 is a schematic diagram that illustrates a calibration unit 110 configured to receive an endoscope 100 and configured to calibrate a sensor 104 associated with the endoscope 100, according to an embodiment of the invention. The calibration unit 110 has an active calibration component 112 and a calibration control module 118. The sensor 104 associated with the endoscope 100 (also referred to as an endoscopic sensor 104) is an EM radiation sensor or other type of sensor configured to function as an image detector (e.g., a charge-coupled device (CCD), a pixel array) that can be associated with a lens or set of lenses. The endoscopic sensor 104 can be calibrated based on a calibration procedure when at least a portion of the endoscope 100, such as a distal end portion 102 of the endoscope 100, is coupled to (e.g., received within an opening of) the calibration unit 110.

The active calibration component 112 is configured to define a calibration target in response to a calibration instruction associated with, for example, the endoscopic sensor 104 and/or a calibration procedure. The active calibration component 112, in some embodiments, can include an EM radiation source such as a single point illuminator (e.g., light emitting diode (LED), halogen light, incandescent light) and/or a display such as a liquid crystal display (LCD). The EM radiation source can be configured to emit EM radiation defining a calibration target towards the endoscopic sensor 104 during a calibration procedure associated with the endoscopic sensor 104 when the endoscope 100 is coupled to the calibration unit 110.

The active calibration component 112 can be configured to define a variety of calibration targets (also referred to as a target or a calibration target image) such as, for example, any combination of a uniform white field at any color temperature, a uniform black field, a uniform color field having a specified color (e.g., a band of wavelengths centered around red, or green, etc.) or range of colors, a bore sighting image (e.g., concentric circles to estimate astigmatism), an image for calibrating resolution, an image used for lens aberration correction, and an advanced spectral imaging calibration target, etc. In some embodiments, the EM radiation source can be used to define a calibration target by emitting EM radiation, for example, onto a screen (not shown) disposed within an enclosure defined by the calibration unit 110.

In some embodiments, the active calibration component 112 can have a portion (e.g., static calibration image, calibration target defined by an EM radiation source) configured to move between one or more positions within the calibration unit 110 via an actuator (not shown). An example of an active calibration component having a portion configured to move via an actuator is discussed in connection with FIG. 3.

Figure 2:
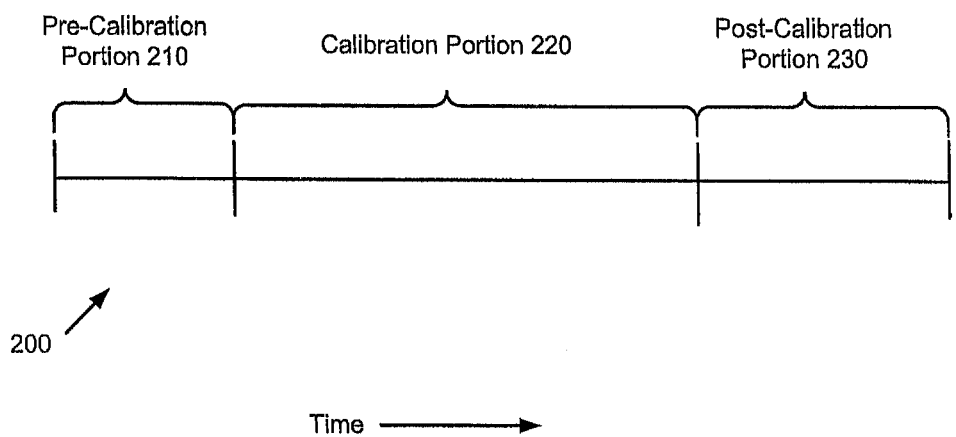
FIG. 2 is a schematic diagram illustrating a timeline of a calibration procedure that can be implemented using the calibration unit shown in FIG. 1, according to an embodiment of the invention.

The active calibration component 112, can be modified during, any time before, and/or any time after a pre-calibration portion, a calibration portion, and/or a calibration test portion associated with a calibration procedure. FIG. 2 is a schematic diagram illustrating a timeline of a calibration procedure 200 that can be implemented using the calibration unit 110 shown in FIG. 1, according to an embodiment of the invention. The timeline of the calibration procedure 200 includes a pre-calibration portion 210, a calibration portion 220, and a post-calibration portion 230.

The pre-calibration portion 210 can include, for example, execution of a start-up algorithm for the calibration unit 110 and/or initialization/resetting of components (e.g., active calibration component 112) associated with the calibration unit 110. The pre-calibration portion 210 can be triggered, for example, in response to the endoscope 100 being coupled to the calibration unit 110.

The calibration portion 220 can include, for example, execution of one or more calibration algorithms (e.g., a multi-point calibration algorithm) for calibrating the endoscopic sensor 104. A calibration algorithm can include defining a calibration target using the active calibration component 112, receiving/collecting data associated with the endoscopic sensor 104 based on the calibration target, and/or calculating one or more correction factors associated with the endoscopic sensor 104. The calibration algorithm can be, for example, a reduced noise calibration algorithm performed at different light levels (e.g., greater than or equal to zero light intensity) and/or a calibration algorithm associated with a specified spectral region of EM radiation. The correction factor(s) can be, for example, a linear luminance correction factor(s), a color gain correction factor(s), a white balance correction factor(s), a resolution correction factor(s), and/or a lens aberration (e.g., pincushion distortion, barrel distortion) correction factor(s).

In some embodiments, different portions of the endoscope 100 can be calibrated serially or in parallel during the calibration portion 220 of the calibration procedure timeline 200. The different portions can be, for example, different image-detecting elements (not shown) within the endoscopic sensor 104 and/or different sensors (not shown) of the endoscope 100. The different image-detecting elements (e.g., pixels) can be individually calibrated to have a target responsiveness or to produce a target response using the calibration unit 110. The different image-detecting elements can be associated with different spectral regions of EM radiation. The different portions of the endoscope 100 can be calibrated using different calibration algorithms during the calibration portion 220 of the calibration procedure timeline 200.

The post-calibration portion 230 can include, for example, verification of the accuracy of one or more correction factors calculated during the calibration portion 220 of a calibration procedure. The accuracy of the correction factor(s) can be determined based on test calibration targets defined by the active calibration component 112. The post-calibration portion 230 can include, for example, a determination that the endoscope 100 is operating according to a specification and/or is capable of supporting a clinical application (e.g., has sufficient resolution for a particular clinical application). More details related to calibration procedures are discussed in connection with the flowcharts shown in FIGS. 4 and 5.

During each of the portions 210, 220, and 230 of the calibration procedure, a control loop(s) (e.g., a feedback loop, feedforward loop) can be implemented by the calibration control module 118 based on signals from sensors 104 associated with the endoscope 100 and/or calibration unit 110. For example, during the calibration portion 220 a feedback loop can be implemented such that the intensity level of a calibration target image defined by the active calibration component 112 can be held substantially at a specified set point. The time constants of the control loop can be defined and/or adjusted to avoid changes that could adversely affect calibration of the endoscopic sensor 104. In some embodiments, the time constants associated with the control loops can be based on the responsiveness of the endoscopic sensor 100. More details related to control loops and signals from sensors are discussed in connection with FIG. 3.

In some embodiments, the calibration procedure associated with the calibration procedure timeline 200 can include additional and/or different portions having a different order than those shown in FIG. 2. For example, in some embodiments, a calibration procedure can include, for example, only a post-calibration portion and not a calibration portion. In some embodiments, a calibration procedure can include a post-calibration test after each sensor from a multi-sensor endoscope has been calibrated. In some embodiments, an endoscope(s) can be calibrated using a calibration procedure before being used in a clinical application and later re-calibrated with the calibration procedure (or a different calibration procedure) during an intermediate portion of the clinical application.

Referring back to FIG. 1, the calibration control module 118 can be configured to control at least a portion of the calibration unit 110, such as the active calibration component 112, and/or at least a portion of the endoscope 100 during a calibration procedure associated with the endoscopic sensor 104. For example, in some embodiments, the active calibration component 112 can be triggered to define a calibration target image in response to a signal from the calibration control module 118 during a calibration procedure (e.g., based on one or more instructions associated with the calibration procedure). The calibration control module 118 can also trigger the endoscopic sensor 104, for example, to capture a frame of the calibration target image defined by the active calibration component 112.

The calibration control module 118 can also be configured to process data associated with the calibration unit 110 and/or the endoscope 100 during a calibration procedure. For example, the calibration control module 118 can process data received from the endoscope 100 and/or data associated with the active calibration component 112, for example, to calculate one or more correction factors associated with the endoscopic sensor 104. Data received from the endoscope 100 can also be processed by the calibration control module 118, for example, during a post-calibration test to determine the accuracy of a correction factor calculated during a calibration portion of a calibration procedure.

In some embodiments, the calibration control module 118 can be a hardware-based module (e.g., processor, application-specific integrated circuit (ASIC), field programmable gate array (FPGA), read-only memory (ROM)) and/or software-based module (e.g., set of instructions executable at a processor, software code). For example, the calibration control module 118 can have a processor (not shown) configured to access a calibration instruction from a memory (not shown) associated with the calibration control module 118. The processor can be configured to send and/or receive signals to trigger the active calibration component 112 to define a calibration target at different times during the calibration procedure. The processor can also be configured to send and/or receive signals to trigger the endoscopic sensor 104 to capture frames and/or send signals/data at different times during the calibration procedure.

In some embodiments, the calibration unit 110 can be configured to receive and detect different types of endoscopes (not shown) that may have one or more different sensors and/or calibration requirements (e.g., specified environmental conditions, specified calibration limits) that can be associated with operating conditions within, for example, a clinical application. In some embodiments, the calibration control module 118 can be configured to, for example, detect an endoscope type when, for example, the endoscope is inserted into the calibration unit 110 for calibration. The calibration control module 118 can be configured to, for example, select and/or execute, based on the endoscope type, one or more calibration instructions from a library of calibration instructions. The active calibration component 112 can be controlled (e.g., triggered to define a calibration target, moved) and/or the endoscope of the particular type can be triggered to perform a function based on the calibration instruction.

In some embodiments, one or more functions associated with the calibration control module 118 can be performed outside of the calibration unit 110. For example, in some embodiments, one or more calibration instructions can be executed by and/or stored at a calibration control module (not shown) disposed outside of the calibration unit 110. The calibration control module can be included in, for example, a computer system (e.g., personal computer, database, control server) in communication with the calibration unit 110 via, for example, a wired and/or wireless network (not shown). In these embodiments, the calibration unit 110 can be optionally configured without one or more portions or functionalities of the calibration control module 118.

In some embodiments, one or more portions of the active calibration component 112 can be disposed outside an enclosure (not shown) defined by the calibration unit 110. For example, in some embodiments, one or more portions of the active calibration component 112 can be disposed outside of the calibration unit 110 or controlled (e.g., moved) using a controller disposed outside of the calibration unit 110. In some embodiments, the calibration unit 110 can include more than one active calibration component (not shown).

In some embodiments, an adapter (not shown in FIG. 1) can be disposed between the endoscope 100 and the calibration unit 110. For example, the adapter can be used to mate the distal end portion 102 of the endoscope 100 with the calibration unit 110 such that the endoscopic sensor 104 can have a specified position (e.g., distance, orientation) relative to a portion of the active calibration component 112. More details related to adapters associated with a calibration unit and/or an endoscope are discussed in connection with FIGS. 6 through 13.

Figure 3:
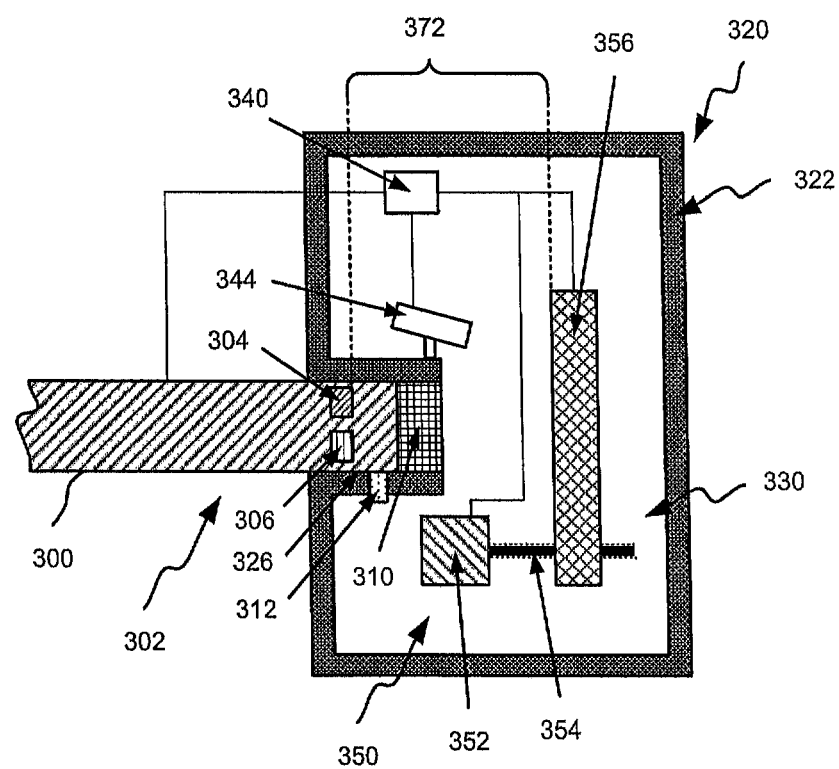
FIG. 3 is a schematic block diagram of a side cross-sectional view of an endoscope and a calibration unit configured for calibration of the endoscope, according to an embodiment of the invention.

FIG. 3 is a schematic block diagram of a side cross-sectional view of a calibration unit 320 configured for calibration of an endoscope 300, according to an embodiment of the invention. The endoscope 300 has a light source 304 and an image detector 306. The calibration unit 320 and endoscope 300 are configured such that the image detector 306 can be calibrated when the endoscope 300 is coupled to the calibration unit 320.

As shown in FIG. 3, the calibration unit 320 is an enclosure that includes an active calibration component 330, a calibration control module 340, and a sensor (e.g., a photodetector) 344. The calibration control module 340 is in communication with the endoscope 300 such that the calibration control module 340 can trigger the endoscope 300 to, for example, capture an image and/or send data to the calibration control module 340 during a calibration procedure. The calibration control module 340 is also in communication with the active calibration component 330 such that the calibration control module 340 can trigger the active calibration component 330 to, for example, define a calibration target based on a calibration procedure associated with the image detector 306.

As shown in FIG. 3, at least a portion of a distal end portion 302 of the endoscope 300 has been received into an opening 326 of the calibration unit 320 and is in contact (or near contact) with a window 310 that is substantially transparent to one or more spectral regions of EM radiation. In some embodiments, the endoscope 300 is configured to contact (or nearly contact) the window 310 such that small imperfections associated with the window 310 may not be perceptible to the image detector 306 (e.g., out of focus) during calibration, and thus, may not affect calibration of the image detector 306.

In some embodiments, the window 310 can be configured to have a specified thickness and the distal end portion 302 of the endoscope 300 can be configured to abut (or nearly contact) the window 310 such that distance 372 between the image detector 306 and an EM radiation source 356 (described below) can be a specified distance during calibration of the image detector 306. In some embodiments, the calibration unit 320 can have a stop (e.g., protrusion, pin) or set of blocking components that can be used to ensure that the image detector 306 is a specified distance 372 from the calibration target. In some embodiments, the calibration unit 320 can have a sensor (not shown) configured to detect the distance 372 of the image detector 306 relative to the EM radiation source 356. The detected distance 372 can be used to, for example, select and/or modify a calibration procedure.

The endoscope 300 is received by the calibration unit 320 such that an environment within the calibration unit 320 can be substantially controlled during calibration of the image detector 306. For example, the distal end portion 302 of the endoscope 300 and the calibration unit 320 can be configured to mate such that the environment outside of the calibration unit 320 (e.g., ambient light, debris, air) is substantially prevented from entering the enclosure defined by the walls 322 of calibration unit 320 during calibration of the image detector 306. Although not shown, a sealing mechanism (not shown) such as an o-ring can be disposed between the endoscope 300 and the calibration unit 320 to substantially prevent influence from the ambient environment during calibration of the image detector 306.

The calibration unit 320 also optionally includes a sensor 312 (can be referred to as a placement sensor) to determine whether or not the endoscope 300 (e.g., the distal end portion 302) is present or has been inserted in a desirable manner (e.g., fully inserted) into the calibration unit 320. In some embodiments, the sensor 312 can be used to trigger execution of any portion of a calibration procedure, for example, when the presence of the endoscope 300 is detected. In some embodiments, the sensor 312 can be used to trigger termination of any portion of a calibration procedure, for example, when the endoscope 300 is prematurely removed during the calibration procedure. In some embodiments, the sensor 312 can be a non-contact sensor.

Although in this embodiment, the endoscope 300 has been inserted into the opening 326 of the calibration unit 320, in some embodiments, a calibration unit (not shown) can be configured to receive a distal end portion of an endoscope (not shown) on an outside portion of the calibration unit. For example, the endoscope can be coupled to the calibration unit using a latch and/or another mechanism (e.g., locking mechanism). The endoscope can be coupled to a seal of the calibration unit to substantially prevent, for example, ambient light and/or air from entering the calibration unit 320 during a calibration procedure associated with the endoscope.

As shown in FIG. 3, the active calibration component 330 includes the EM radiation source 356 and an actuator 350 configured to move the EM radiation source 356. The EM radiation source 356 can be an LCD screen. The actuator 350 includes a motor 352 coupled to and configured to rotate a threaded screw 354 about a longitudinal axis of the threaded screw 354. The EM radiation source 356 is coupled to the threaded screw 354 via a threaded collar (not shown) such that the EM radiation source 356 can be moved along the longitudinal axis of the threaded screw 354 when the threaded screw 354 is rotated. In particular, the actuator 350 is configured to move the EM radiation source 356 relative to the image detector 306 such that, for example, the distance 372 between EM radiation source 356 and the image detector 306 is at a desired setting during a particular portion of a calibration procedure associated with the image detector 306. In some embodiments, the distance 372 can be defined to accommodate calibration of a specified range of working distances, a specified field of view, and/or zoom optics (not shown) associated with the image detector 306.

Although not shown, an actuator can be configured to modify the angle of the EM radiation source 356 relative to, for example, the longitudinal axis of the endoscope 300. In some embodiments, an actuator (not shown) can be configured to move the EM radiation source 356 based on a pulley system or a mechanism having gears. The EM radiation source 356 can be, in some embodiments, replaced with a static calibration target image (not shown) such as a printed image defined for use in a calibration procedure.

In some embodiments, the window 310 can be configured to filter and/or diffuse one or more spectral region(s) of EM radiation during calibration of the image detector 306. For example, the window 310 can be configured such that the window 310 is substantially transparent to spectral regions of EM radiation that can be detected by the image detector 306. In some embodiments, calibration unit 320 can be configured such that the window 310 is a removable window 310 that can be replaced, for example, when scratched, cracked, and/or a different filtering window (not shown) is desired during calibration of the image detector 306 (or an image detector of a different endoscope coupled to the calibration unit 320). In some embodiments, an additional static target, screen, and/or filter (not shown) can be disposed between the endoscope 300 and any portion of the active calibration component 330 during calibration.

As shown in FIG. 3, the calibration unit 320 has the photodetector 344 configured to detect EM radiation within the calibration unit 320. In this embodiment, the photodetector 344 is in communication with the calibration control module 340. One or more signals from the photodetector 344 can be used by the calibration control module 340, for example, in a feedback loop to control the spectral characteristics and/or the intensity of calibration target images defined by the EM radiation source 356.

In some embodiments, one or more signals from the photodetector 344 can be used, for example, by the calibration control module 340 to control operation of the endoscope 300 during a calibration procedure. For example, signals from the photodetector 344 can be used in a control loop (e.g., feedback loop) to modify light (or more generally EM radiation) emitted from the light source 304 (if the light source 304 is used during a calibration procedure). Signals from the photodetector 344 can be used to calibrate, for example, an aperture (not shown) associated with the endoscope 300.

In some embodiments, the calibration unit 320 can have a variety of sensors such as a temperature sensor (not shown) and/or a pressure sensor (not shown). The temperature sensor and/or pressure sensor can be used by the calibration control module 340 to monitor/control the environment within the calibration unit 320 and/or any portion of the active calibration component 330 during a calibration procedure. The temperature within the calibration unit 320 can be adjusted using, for example, a heating/cooling element (not shown). The pressure within the calibration unit 320 can be adjusted using, for example, a valve system (not shown) or pump (not shown).

In some embodiments, the calibration unit 320 can be configured to calibrate a sensor other than the image sensor 306, For example, the calibration unit 320 can be configured to calibrate the light source 304, a temperature sensor (not shown), or a pressure sensor (not shown) associated with the endoscope 300.

Although not shown, the calibration unit 320 can have one or more input ports, output ports, and/or antennas, that can be used for communication with, for example, the endoscope 300. In some embodiments, the endoscope 300 can be configured to communicate with the calibration control module 340 via a wired communication link and/or a wireless communication link. Although in this embodiment the calibration control module 340 is in direct communication with the endoscope 300, in some embodiments, the calibration control module 340 is configured to communicate with the endoscope via a separate device (not shown), such as a computer. In some embodiments, the calibration unit 320 can be configured with a display (not shown) or other indicator (not shown) that can be used to communicate instructions to a user of the calibration unit 320.

Figure 4:
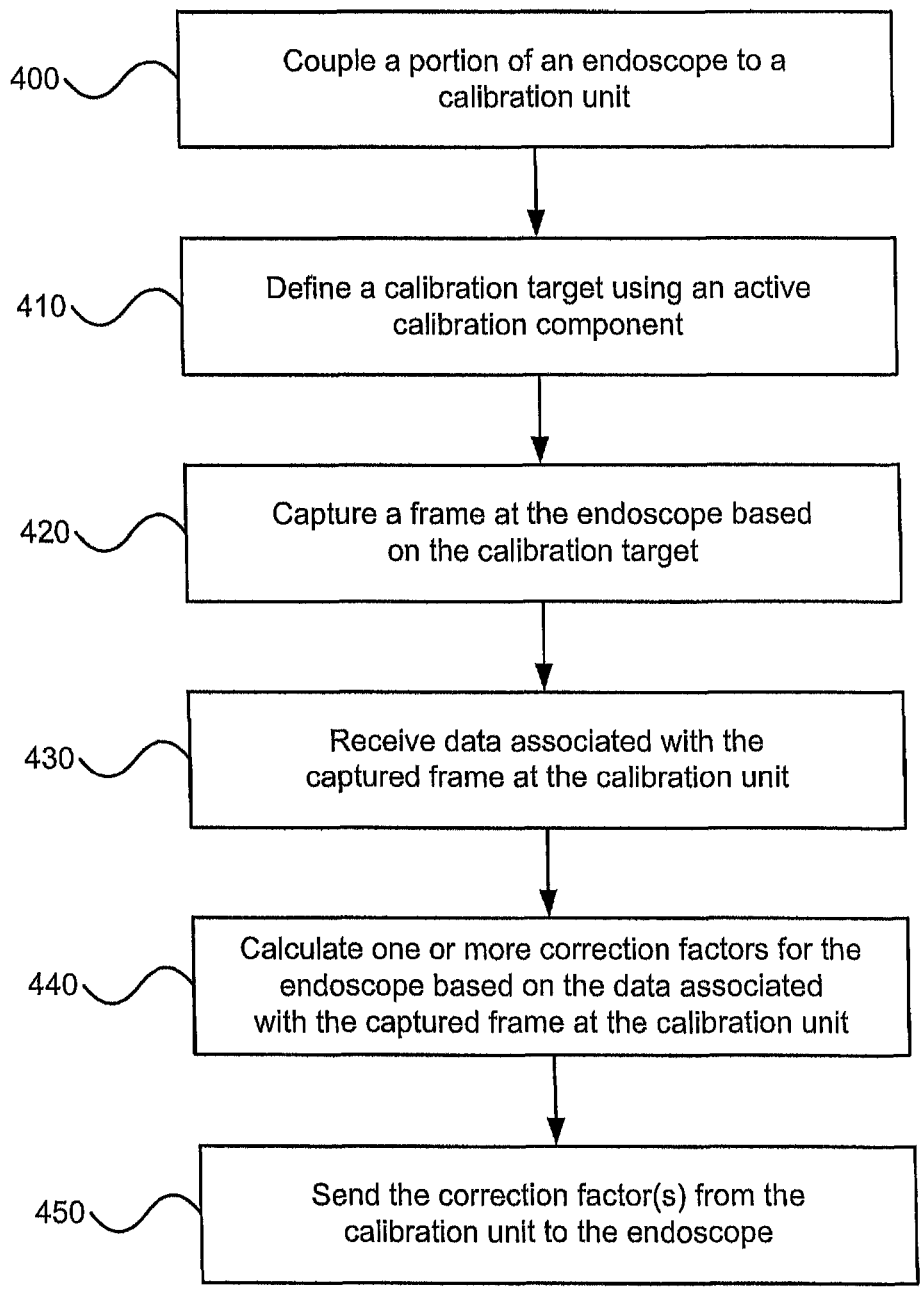
FIG. 4 is a flowchart that illustrates a method for calibrating an endoscopic sensor using an active calibration component of a calibration unit, according to an embodiment of the invention.

FIG. 4 is a flowchart that illustrates a method for calibrating an endoscopic sensor using an active calibration component of a calibration unit, according to an embodiment of the invention. Portions of the method illustrated in the flowchart can be used during any portion of a calibration procedure.

The flowchart illustrates that a portion of an endoscope is coupled to a calibration unit at 400. In some embodiments, a portion of the endoscope can be received within a portion of the calibration unit. The calibration unit can be configured to prompt a user to couple the endoscope to the calibration unit. A communication link between the calibration unit and the endoscope can be established when the endoscope is coupled to the calibration unit. In some embodiments, the calibration unit can be configured to detect whether or not the endoscope has been properly coupled to the calibration unit and an initialization procedure (e.g., procedure for turning-on/warming-up) can be executed.

A calibration target is defined using an active calibration component at 410. The calibration target can be defined by the active calibration component in response to a calibration instruction associated with, for example, a calibration procedure or triggered via input from a user. The calibration target can be defined by, for example, EM radiation emitted from an EM radiation source associated with the active calibration component in a specified arrangement, at a specified intensity, and/or at a specified distance/orientation towards the endoscope.

A frame is captured by an endoscopic sensor associated with the endoscope based on the calibration target at 420. If the calibration target is defined by an EM radiation source, the frame can be captured based on EM radiation emitted towards the endoscopic sensor. The frame can be captured in response to a signal from the calibration unit (e.g., calibration control module). In some embodiments, multiple frames can be captured by the endoscopic sensor. In some embodiments, the frame can be captured by a portion of the endoscopic sensor. In some embodiments, the calibration target can be illuminated by an EM radiation source associated with the endoscope and/or the calibration unit such that the frame can be captured.

Data associated with the captured frame is received at the calibration unit at 430. One or more correction factors can be calculated at the calibration unit based on the data at 440 and/or the correction factor(s) can be sent from the calibration unit to the endoscope at 450. In some embodiments, any of the data processing and correction factor processing associated with blocks 430, 440, and/or 450 can be performed at a calibration control module associated with the calibration unit or a module separate from the calibration unit. In some embodiments, multiple correction factors can be calculated per frame. For example, the correction factors can represent an additive or multiplicative factor to be applied to each pixel in the frame (e.g., so that there can be up to millions of correction factors per frame). The correction factors can be sent from the calibration unit to the endoscope, and applied in real time to streaming data or in a post-processing step. In some embodiments, calculation of a correction factor may not be necessary if the performance of the endoscope meets specified requirements (e.g., threshold conditions).

In some embodiments, any of the blocks associated with the flowchart can be performed at different times, such as in a different order, or repeated within a calibration procedure. For example, a first calibration target can be defined at a first light intensity during a first time period and a frame of the first calibration target can be captured by an endoscope during the first time period. A second calibration target can be defined at a second light intensity during a second time period after the first time period and a frame of the second calibration target can be captured by the endoscope during the second time period. After the frame of the first calibration target and a frame of the second calibration target have been captured, data associated with the frames can then be used to calculate one or more correction factors.

In some embodiments, a control loop such as a feedback loop can be employed during any portion of the flowchart. For example, the calibration unit can be configured to use a feedback signal from a photodetector to maintain a calibration target emitted from an EM radiation sensor associated with an active calibration component at a specified light intensity.

In some embodiments, calibration of the endoscope can be performed to equalize/normalize the responsiveness of the endoscope over time. Accordingly, data from multiple calibrations of the endoscope can be used to calculate a correction factor for the endoscope, if necessary. In some embodiments, calibration of the endoscope can be performed to equalize/normalize the responsiveness of the endoscope with other endoscopes. Accordingly, data from multiple endoscopes can be used to calculate a correction factor for the endoscope, if necessary.

Figure 5:
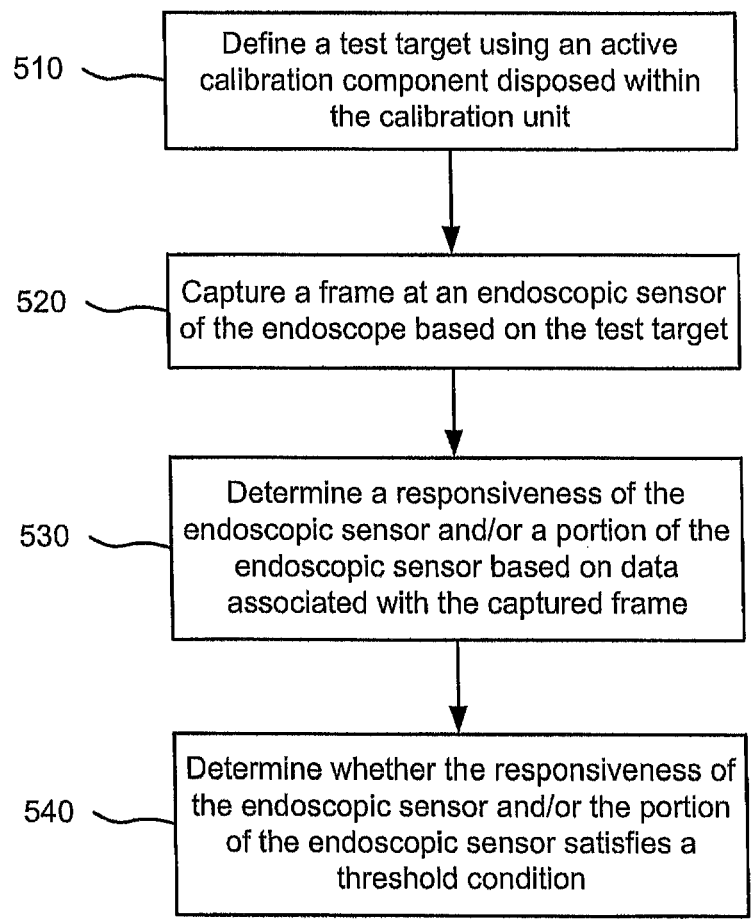
FIG. 5 is a flowchart that illustrates a method for testing an endoscopic sensor using an active calibration component of a calibration unit, according to an embodiment of the invention.

FIG. 5 is a flowchart that illustrates a method for testing an endoscopic sensor using an active calibration component of a calibration unit, according to an embodiment of the invention. Portions of the method illustrated in the flowchart can be used during any portion of a calibration procedure. The method illustrated in FIG. 5 can be implemented, for example, after the method illustrated in FIG. 4 to determine whether or not a correction factor calculated at 440 and applied by the endoscope will enable the endoscopic sensor to satisfy a threshold condition associated with a clinical application.

A test target is defined using an active calibration component disposed within the calibration unit at 510. The test target can be defined by the active calibration component in response to a calibration instruction associated with a calibration procedure. The test target can be analogous or identical to a calibration target. In some embodiments, the test target can be defined by, for example, EM radiation emitted from an EM radiation source associated with the active calibration component towards the endoscope.

A frame is captured at an endoscopic sensor of the endoscope based on the test target at 520. If the test target is defined by an EM radiation source, the frame can be captured based on EM radiation emitted towards the endoscopic sensor. The frame can be captured in response to a signal from the calibration unit (e.g., calibration control module). In some embodiments, multiple frames can be captured by the endoscopic sensor and/or the frame(s) can be captured by a portion of the endoscopic sensor. In some embodiments, the test target can be illuminated by an EM radiation source associated with the endoscope and/or the calibration unit such that the frame can be captured. In some embodiments, the frame can be captured based on a correction factor calculated, for example, based on the method illustrated in FIG. 4.

A responsiveness of the endoscopic sensor and/or a portion of the endoscopic sensor (e.g., a particular set of pixels of an endoscopic sensor) is determined based on data associated with the captured frame at 530. In some embodiments, the data associated with the captured frame can be compared with data associated with (e.g., used to define) the test target. The differences, if any, can be quantified to calculate the responsiveness of the endoscopic sensor. The responsiveness, in some embodiments, can be referred to as a sensitivity. The responsiveness of the endoscopic sensor and/or portions of the endoscopic sensor can be, for example, characterized in terms of a voltage level value(s), a current level value(s), and/or a digital number(s) (DN).

The responsiveness of the endoscopic sensor and/or the portion of endoscopic sensor with respect to a threshold condition is determined at 540. The threshold condition can be based on, for example, an operating condition associated with a clinical application. A notification regarding whether the responsiveness of the endoscopic sensor and/or portion of the endoscopic sensor did or did not satisfy the threshold condition can be sent to, for example, a user or a display. In some embodiments, the EM source can be moved relative to the endoscope based on the data associated with the captured frame and/or the determined responsiveness. In some embodiments, a correction factor can be modified and/or an additional correction factor can be calculated. The modified correction factor and/or additional correction factor can be verified using the method illustrated in FIG. 5.

Figure 6:
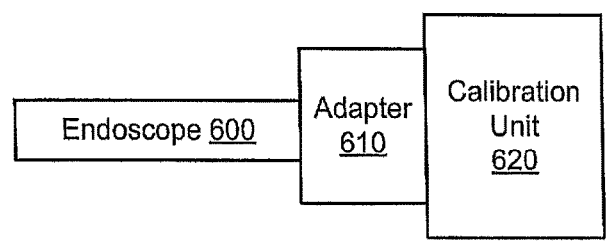
FIG. 6 is a schematic block diagram that illustrates an adapter disposed between an endoscope and a calibration unit, according to an embodiment of the invention.

FIG. 6 is a schematic block diagram that illustrates an adapter 610 disposed between an endoscope 600 and a calibration unit 620, according to an embodiment of the invention. The adapter 610 is configured to be coupled to (e.g., removably coupled to) the calibration unit 620, and the endoscope 610 is configured to be coupled (e.g., removably coupled to) to the adapter 610.

In some embodiments, the endoscope 600, the adapter 610, and the calibration unit 620 can be collectively configured such that the endoscope 600 has a specified position with respect to one or more components of the calibration unit 620 when an endoscopic sensor (not shown) associated with the endoscope 600 is calibrated using the calibration unit 620. The endoscope 600, the adapter 610, and the calibration unit 620 are configured to be coupled such that calibration of the endoscope 600 can be repeated with consistency.

In some embodiments, the endoscope 600, the adapter 610, and the calibration unit 620 can be configured to mate such that outside environmental influences such as ambient light, debris (e.g., dust), and/or air are substantially prevented from entering the enclosure defined by the calibration unit 620 during calibration of an endoscopic sensor associated with the endoscope 600. In other words, the endoscope 600, the adapter 610, and the calibration unit 620 are configured such that an environment within the calibration unit 620 can be substantially controlled during calibration of an endoscopic sensor of the endoscope 600. In some embodiments, a sealing mechanism (not shown) such as an o-ring can be disposed between the endoscope 600, the adapter 610, and/or the calibration unit 620 to substantially prevent influence from the ambient environment during calibration of the endoscope 600.

Although at least a portion of the adapter 610 (as shown in FIG. 6) is disposed outside of the calibration unit 620 when the adapter 610 is coupled to the calibration unit 620, in some embodiments, the adapter 610 and calibration unit 620 are configured such that the adapter 610 is entirely disposed within the calibration unit 620 when the adapter 610 is coupled to the calibration unit 620.

Figure 7:
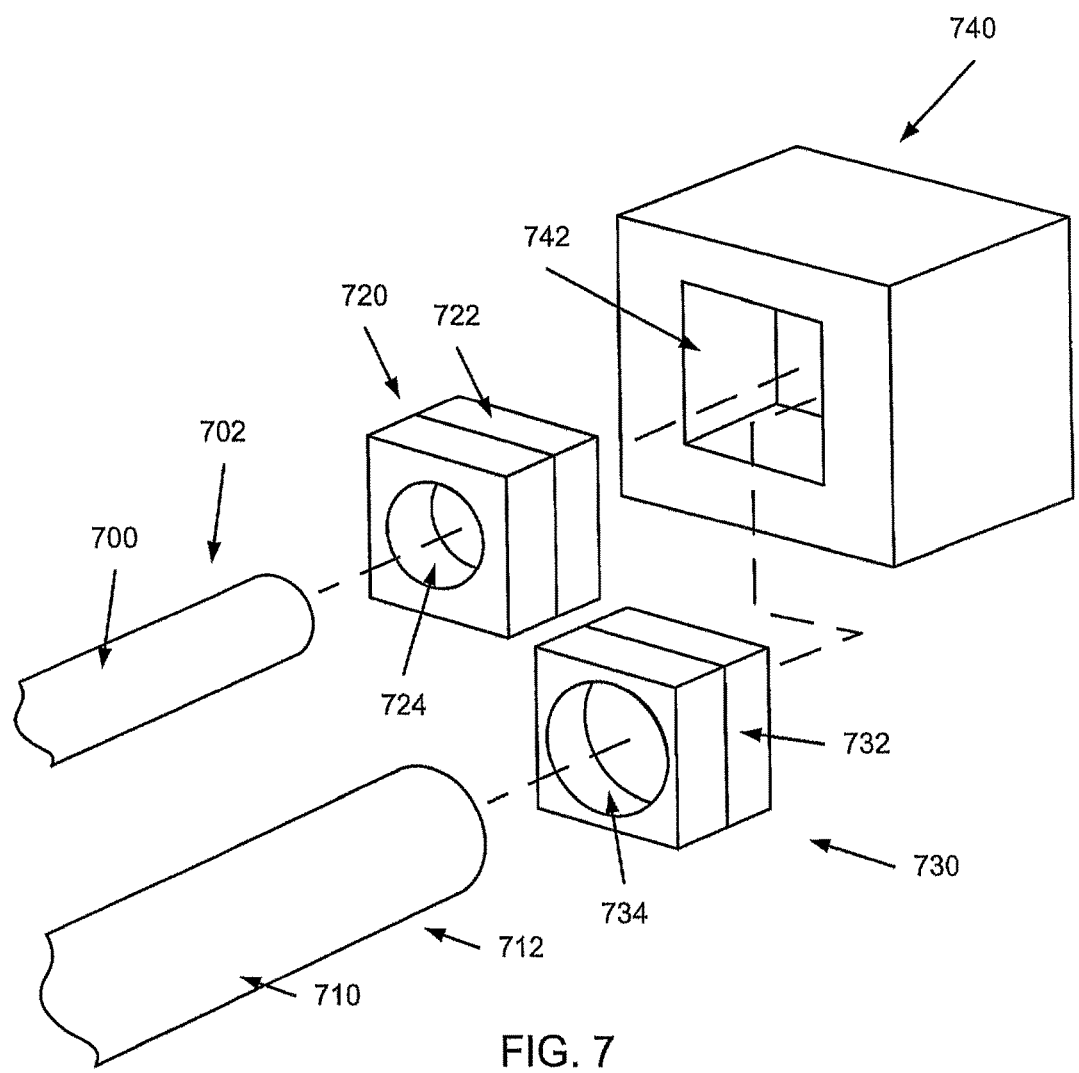
FIG. 7 is a schematic diagram that illustrates a calibration unit, a set of endoscopes, and a set of adapters configured to be coupled to the calibration unit and the respective endoscopes, according to an embodiment of the invention.

FIG. 7 is a schematic diagram that illustrates a set of adapters 720 and 730 configured to be coupled to a calibration unit 740, according to an embodiment of the invention. Adapter 720 has a bore 724 configured to receive a distal portion 702 of an endoscope 700, and adapter 730 has a bore 734 configured to receive a distal portion 712 of an endoscope 710 that has a diameter greater than that of endoscope 700. Although adapter 720 and adapter 730 are configured to receive endoscopes that have different distal diameters (or shapes), adapter 720 and adapter 730 are both configured such that they can be received within an opening 742 of calibration unit 740. Adapters 720 and 730 can include windows 722 and 732, respectively. Each window 722 and 732 can be substantially transparent to one or more spectral regions of EM radiation and can be attached to a substantially opaque part (e.g., which includes the respective bores 724 and 734) that blocks ambient light.

Both endoscope 700 and endoscope 710 can be securely fitted via the adapters 720 and 730, respectively, such that the endoscopes 700 and 710 can be calibrated by the calibration unit 740. The calibration unit 740 can be configured to calibrate endoscope 700 when adapter 720 is inserted into the calibration unit 740 and the endoscope 700 is inserted into the adapter 720. The endoscope 700, the adapter 720, and the calibration unit 740 are configured to fit together such that the ambient environment outside of the calibration unit 740 will substantially be prevented from affecting calibration of endoscope 700 during calibration. Likewise, the calibration unit 740 can be configured to calibrate endoscope 710 when adapter 730 is inserted into the calibration unit 740 and when the endoscope 710 is inserted into the adapter 730. The endoscope 710, the adapter 730, and the calibration unit 740 are configured to fit together such that the ambient environment outside of the calibration unit 740 will substantially be prevented from affecting calibration of endoscope 710 during calibration.

Although the distal portion 702 of the endoscope 700 has a circular shape and the adapter 720 has a corresponding circular bore 724 configured to receive the distal portion 702, in some embodiments, the distal portion 702 of the endoscope 700 and the bore 724 of the adapter can be configured such that the endoscope 700 can only fit into the bore 724 in a finite number of orientations (e.g., one orientation, two orientations). For example, the distal portion 702 of the endoscope 700 can have an oval shape and the bore 724 can have a corresponding oval shape. Likewise, an outside portion of the adapter 720 and the opening 742 of the calibration unit 740 can be configured such that the adapter 720 can only be inserted into the opening 742 of the calibration unit 740 in a finite number of orientations (e.g., one orientation, two orientations).

Figure 8:
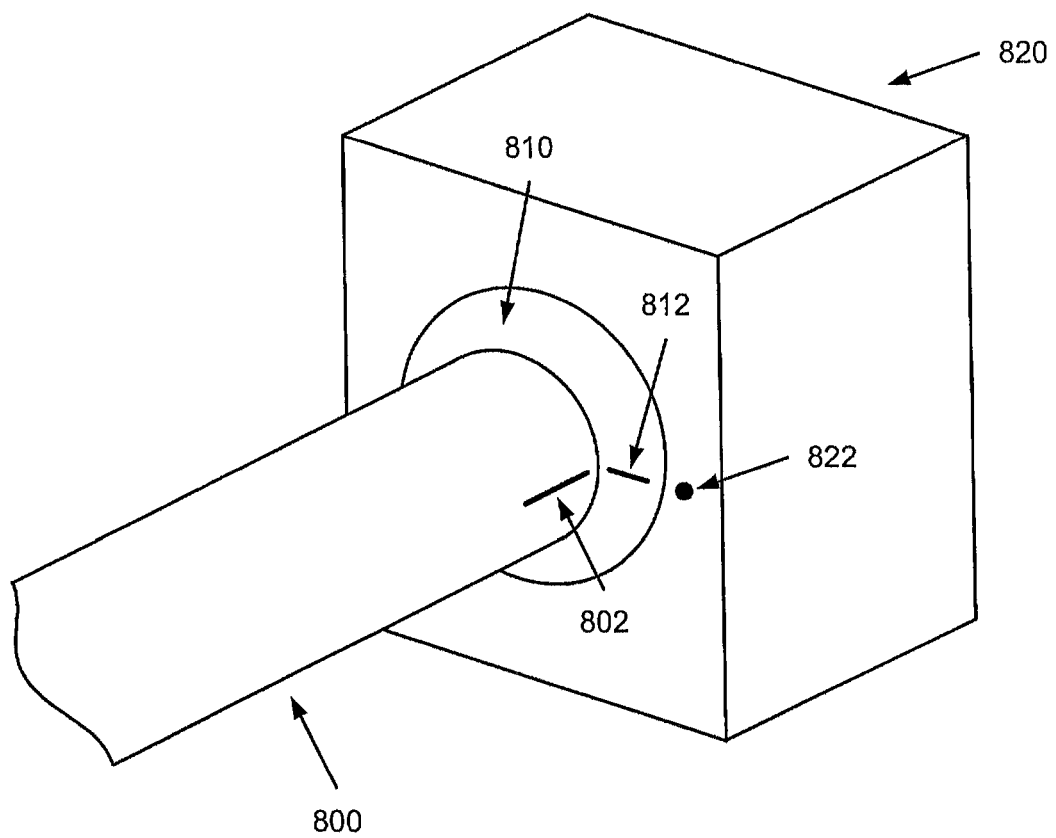
FIG. 8 is a schematic block diagram that illustrates an endoscope received by an adapter that has been received by a calibration unit, according to an embodiment of the invention.

FIG. 8 is a schematic block diagram that illustrates an endoscope 800 received by an adapter 810 that has been received by a calibration unit 820, according to an embodiment of the invention. The endoscope 800 has been inserted into the adapter 810 such that an orientation feature 802 of the endoscope 800 is aligned with an orientation feature 812 of the adapter 810. Also as shown in FIG. 8, the adapter 810 has been inserted into the calibration unit 820 such that the orientation feature 812 of the adapter 810 is aligned with an orientation feature 822 of the calibration unit 820. The orientation features 802, 812, and 822 are configured such that the endoscope 800 (and/or an endoscopic sensor (not shown)) has a specified orientation relative to the calibration unit 820 (and/or a calibration target (not shown)) when the orientation features 802, 812, and 822 are aligned.

In some embodiments, the orientation features 802, 812, and 822 can be configured such that the endoscope 800 has a specified orientation relative to the calibration unit 820 when the orientation features 802, 812, and 822 have a specified orientation with respect to one another (e.g., unaligned orientation). Although in this embodiment the endoscope 800, the adapter 810, and the calibration unit 820 each have an orientation feature, in some embodiments, only the endoscope 800 and calibration unit 820 can have orientation features (not shown) that are configured such that the endoscope 800 has a specified orientation relative to the calibration unit 820 when the orientation features are aligned.

In some embodiments, the number of orientations with which the endoscope 800 can be received by the adapter 810 can be limited (e.g., one, less than three) if the endoscope 800 and the adapter 810 have different shapes than those shown in FIG. 8. Also, the number of orientations with which the adapter 810 can be received by the calibration unit 820 can be limited (e.g., one, less than three) if the adapter 810 and the calibration unit 820 have different shapes than those shown in FIG. 8.

Figure 9:
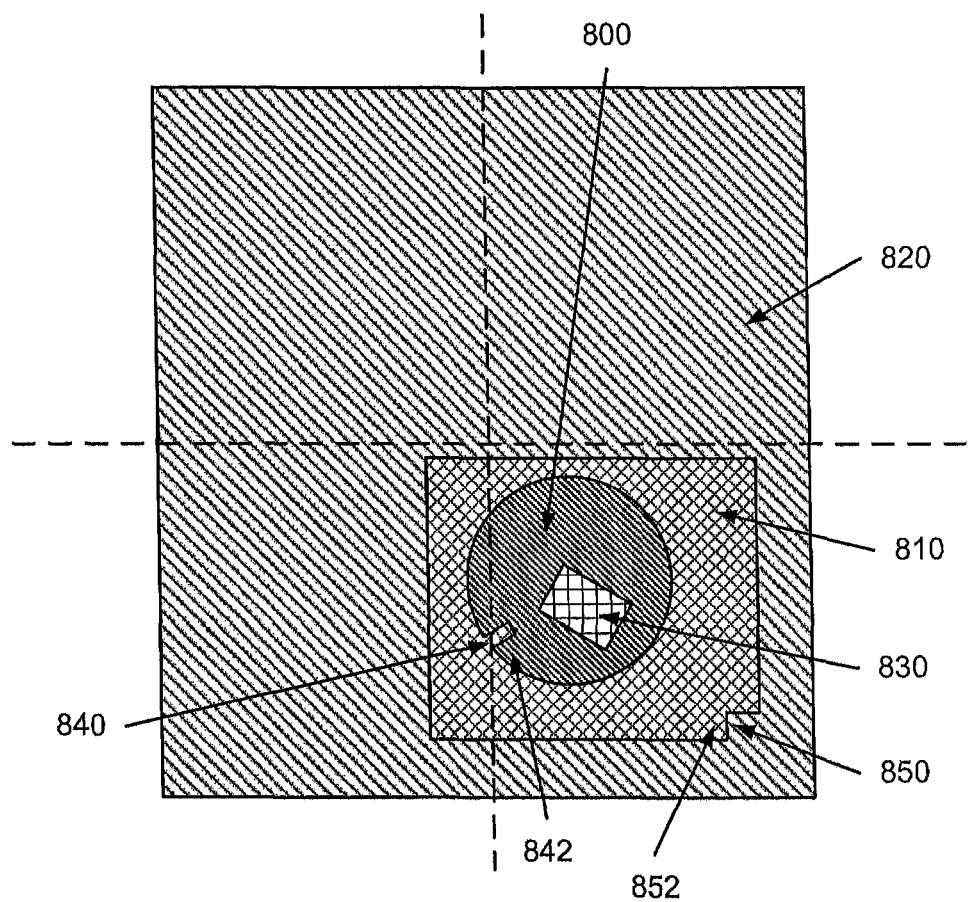
FIG. 9 is a schematic diagram that illustrates a cross-sectional view of an endoscope received by an adapter that has been received by a calibration unit, according to an embodiment of the invention.

FIG. 9 is a schematic diagram that illustrates a cross-sectional view of an endoscope 800 received by an adapter 810 that has been received by a calibration unit 820, according to an embodiment of the invention. In this embodiment, the cross-sectional view is within a plane that is normal to a longitudinal axis of the endoscope 800. The adapter 810 can be received by the calibration unit 820 in the orientation shown in FIG. 9 when the orientation feature 852 of the adapter 810 is mated with orientation feature 850 of the calibration unit 820. Similarly, the endoscope 800 can be received by the calibration unit in the orientation shown in FIG. 9 when orientation feature 842 of the endoscope 800 is mated with the orientation feature 840 of the adapter 810. The orientation features 840, 842, 850, and 852 can be configured such that an endoscopic sensor 830 has a specified orientation relative to a component (not shown) associated with the calibration unit 820 when coupled as shown in FIG. 9.

As shown in FIG. 9, the adapter 810 is received by the calibration unit 820 such that the cross-sectional area of the adapter 810 is outside of the center of the calibration unit 820 as indicated by the intersection of the dashed lines. Also as shown in FIG. 9, the endoscope 800 is received by the adapter 810 such that the cross-sectional area of the endoscope 800 is offset from the center of the adapter 810.

Figure 10:
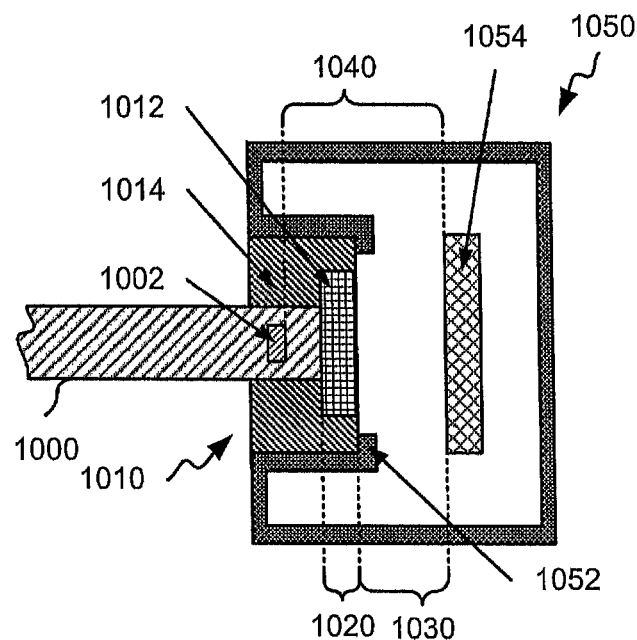
FIG. 10 is a schematic block diagram of a side cross-sectional view of an endoscope received by an adapter that has been received by a calibration unit, according to an embodiment of the invention.

FIG. 10 is a schematic block diagram of a side cross-sectional view of an endoscope 1000 received by an adapter 1010 that has been received by a calibration unit 1050, according to an embodiment of the invention. The distance 1040 between an endoscopic sensor 1002 and a calibration component 1054 (e.g., active calibration component, calibration target) is defined by a thickness 1020 of a window 1012 of the adapter 1010 and a distance 1030. The distance 1030 is the distance between the distal side of window 1012 of the adapter 1010 and the proximal side of calibration component 1054 when the adapter 1010 is inserted into the calibration unit 1050 until the adapter 1010 is in contact with (or near contact with) a protrusion 1052 of the calibration unit 1050. In some embodiments, the endoscopic sensor 1002 can be calibrated by the calibration unit 1050 when the endoscope 1000 is received by the adapter 1010 and the adapter 1010 has been received by the calibration unit 1050 as shown in FIG. 10.

In some embodiments, the thickness 1020 of the window 1012 of the adapter 1010 and/or the protrusion 1052 can be configured such that the distance 1040 between the endoscopic sensor 1002 and the calibration component 1054 is different than that shown in FIG. 10. In some embodiments, the distance 1040 can be defined based on the type of endoscope 1000 and/or the type of endoscopic sensor 1002.

In some embodiments, the adapter 1010 can be an adjustable adapter. For example, the window 1012 can be removably coupled to the adapter 1010 such that the window 1012 can be removed and replaced with a window (not shown) that has a different thickness, shape and/or spectral characteristics. Thus, the endoscopic sensor 1002, for example, can have a different position relative to the calibration component 1054 when the endoscope 1000 is inserted into the adapter 1010 and the adapter 1010 is inserted into the calibration unit 1050. In some embodiments, a body portion 1014 of the adapter 1010 can be replaced with a body portion (not shown) that has a different size and/or shape such that the endoscope 1000 can be in a different position relative to any portion of the calibration unit 1050 when the endoscope 1000 is inserted into the adapter 1010 and the adapter 1010 is inserted into the calibration unit 1050. Although the adapter 1010 in this embodiment has a window 1012 and a body portion 1014, in some embodiments the adapter 1010 can be constructed of a single material (e.g., same material as the window 1012, same material as the body portion 1014) or multiple materials.

Figure 11:
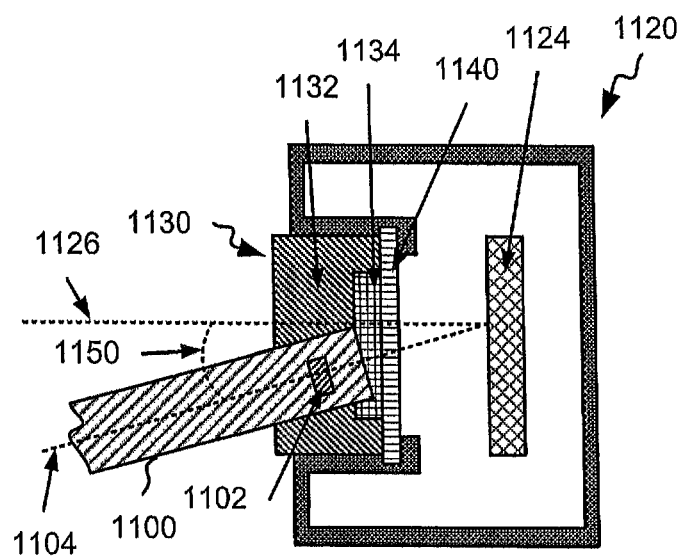
FIG. 11 is a schematic block diagram of a side cross-sectional view of an endoscope received by an adapter that has been received by a calibration unit, according to an embodiment of the invention.

FIG. 11 is a schematic block diagram of a side cross-sectional view of an endoscope 1100 received by an adapter 1130 that has been received by a calibration unit 1120, according to an embodiment of the invention. The adapter 1130 includes a body portion (e.g., an endoscope holder) 1132 for receiving the endoscope 1100. The adapter 1130 is configured such that a longitudinal axis 1104 of the endoscope 1100 has a specified angle 1150 relative to a direction 1126 normal to a plane associated with a calibration component 1124 when the endoscope 1100 is received by the adapter 1130 as shown in FIG. 11. Thus, the endoscopic sensor 1102 has a specified orientation relative to the calibration component 1124. In some embodiments, the calibration component 1124 can be an active calibration component or a calibration target.

In some embodiments, the angle 1150 can be defined to accommodate a calibration requirement associated with the endoscopic sensor 1102. For example, the angle 1150 can be defined to enable calibration of the endoscopic sensor 1102 at a specified angle of incidence with respect to, for example, EM radiation emitted from an EM radiation source (not shown) of the calibration component 1124. In some embodiments, the position and/or orientation of calibration component 1124 can be varied, for example, so that the longitudinal axis 1104 of the endoscope 1100 is substantially parallel to the direction 1126 normal to the plane associated with the calibration component 1124.

As shown in FIG. 11, the calibration unit 1120 has a window 1140 and the adapter has a window 1134 configured to contact (or nearly contact) the window 1140 when the adapter 1130 is coupled to the calibration unit 1120. The endoscope 1100 is configured to contact (or nearly contact) the window 1134 when inserted into the adapter 1130. In some embodiments, these components are configured to contact (or nearly contact) each other such that small imperfections associated with the window 1134 and/or the window 1140 may not be perceptible to the endoscopic sensor 1102 (e.g., out of focus) during calibration, and thus, may not affect calibration of the endoscopic sensor 1102. The window 1140 can be removably coupled to the calibration unit 1120 such that the window 1140 can be replaced, if necessary. In some embodiments, the window 1140 of the calibration unit 1120 can be substantially transparent to one or more specified spectral regions of EM radiation. The window 1134 of the adapter 1130 can also be substantially transparent to the spectral region(s) of EM radiation or a different spectral region(s) of EM radiation.

Figure 12:
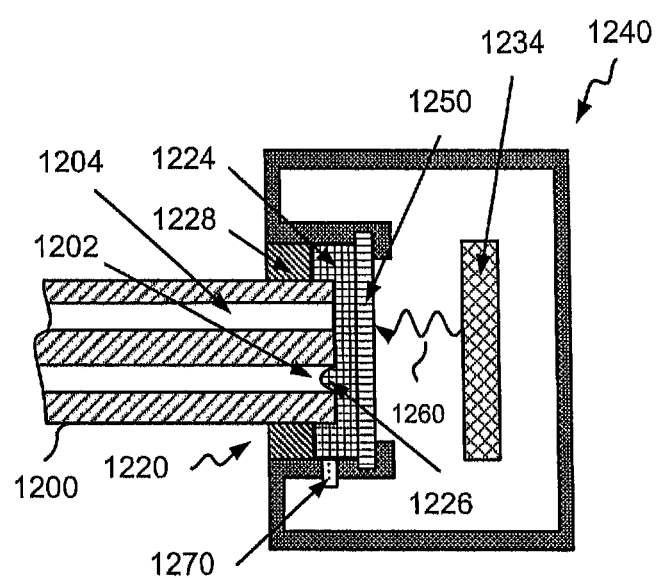
FIG. 12 is a schematic block diagram of a side cross-sectional view of an endoscope received by an adapter that has been received by a calibration unit, according to an embodiment of the invention.

FIG. 12 is a schematic block diagram of a side cross-sectional view of an endoscope 1200 received by an adapter 1220 that has been received by a calibration unit 1240, according to an embodiment of the invention. The calibration unit 1240 has a calibration component 1234 that can be an active calibration component or a calibration target configured for use during calibration of an endoscopic sensor (not shown) of the endoscope 1200. The endoscope 1200 has a lumen 1204 (e.g., channel) that can include, for example, a fiber optic configured to facilitate transmission of EM radiation 1260 emitted from or reflected from the calibration component 1234 towards the endoscope 1200. The endoscopic sensor (not shown) can be configured to receive the EM radiation 1260 via the lumen 1204.

The adapter 1220 is configured such that an opening 1202 of the endoscope 1200 can be removably coupled to a protrusion 1226 of the adapter 1220 such that the endoscope 1200 has a specified orientation relative to the calibration unit 1240. In this embodiment, the protrusion 1226 is defined by a portion of a window 1224 of the adapter 1220, but in some embodiments, the protrusion 1226 can be defined by a different portion of the adapter 1220 (e.g., body portion or endoscope holder 1228). In some embodiments, the protrusion 1226 can have a different shape and can be configured to be inserted into a different portion of the endoscope 1200.

As shown in FIG. 12, the calibration unit 1240 has a window 1250. The calibration unit 1240 also has a sensor 1270 configured to send a signal that can be used to determine whether or not the adapter 1220 and/or endoscope 1200 have been inserted into a desirable position within the calibration unit 1240. In some embodiments, the calibration unit 1240 can have more than one sensor (not shown) configured to detect the position of the adapter 1220 and/or endoscope 1200 relative to the calibration unit 1240.

Figure 13:
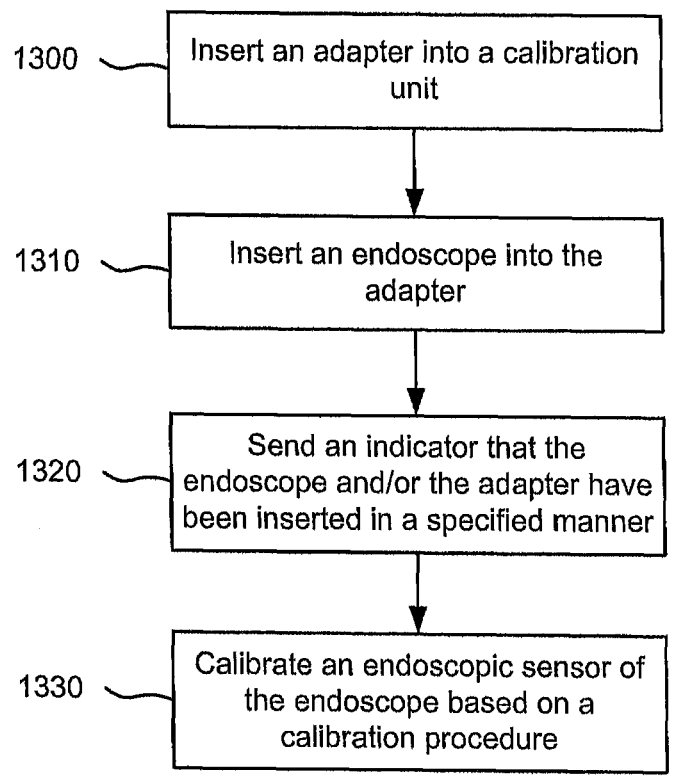
FIG. 13 is a flowchart that illustrates a method for coupling an adapter to a calibration unit and coupling an endoscope to the adapter, according to an embodiment of the invention.

FIG. 13 is a flowchart that illustrates a method for coupling an adapter to a calibration unit and coupling an endoscope to the adapter, according to an embodiment of the invention. An adapter is inserted into a calibration unit at 1300, and an endoscope is inserted into the adapter at 1310. An indicator that the endoscope and/or the adapter have been inserted in a specified manner is sent at 1320. The indicator can be sent from a sensor and received at, for example, a calibration control module.

An endoscopic sensor is calibrated based on a calibration procedure at 1330. The calibration procedure can have more than one calibration instruction and can be initiated in response to the endoscope being inserted into the adapter. The calibration procedure can be executed by a calibration control module disposed within or outside of the calibration unit.

In some embodiments, the blocks in the flowchart shown in FIG. 13 can be performed in a different order. For example, the endoscope can be inserted into the adapter before the adapter is inserted into the calibration unit. In some embodiments, the adapter can be coupled to the calibration unit based on one or more orientation features associated with the adapter and/or the calibration unit. In some embodiments, the endoscope can be coupled to the adapter based on one or more orientation features associated with the endoscope and/or the adapter. The orientation features can be, for example, a protrusion, a notch, and/or a mark.

In an embodiment, an apparatus can include an enclosure configured to receive an endoscope having an electromagnetic radiation sensor. The apparatus can also have an electromagnetic radiation source that has at least a portion disposed within the enclosure and is configured to emit electromagnetic radiation based on a calibration instruction such that the electromagnetic radiation sensor receives at least a portion of the electromagnetic radiation when at least a portion of the endoscope is coupled to the enclosure.

In some embodiments, the enclosure can be configured to prevent electromagnetic radiation produced outside of the enclosure from being received by the electromagnetic radiation sensor when the portion of the endoscope is coupled to the enclosure. In some embodiments, the electromagnetic radiation sensor can be configured to produce a signal based on the portion of the electromagnetic radiation and the apparatus can also includes a processor configured to determine a correction factor associated with the electromagnetic radiation sensor based on the signal.

In some embodiments, the electromagnetic radiation can define a first calibration target and the electromagnetic radiation sensor can be configured to produce a signal based on the first calibration target. The apparatus can also have a processor configured to trigger the electromagnetic radiation source to emit electromagnetic radiation defining a second calibration target in response to the signal.

In some embodiments, the electromagnetic radiation source can be configured to emit electromagnetic radiation at a first time and the portion can be a first portion. The apparatus also can include a detector configured to produce a signal based on an intensity level associated with at least a second portion of the electromagnetic radiation received at the detector. The apparatus also can include a processor configured to trigger the electromagnetic radiation source to emit electromagnetic radiation at a second time different than the first time based on the signal.

In some embodiments, the calibration instruction can be a first calibration instruction and the apparatus can further include an actuator coupled to the electromagnetic radiation source. The actuator can be configured to move the electromagnetic radiation source relative to the endoscope based on a second calibration instruction.

In some embodiments, the endoscope can be a first endoscope and the calibration instruction can be associated with the first endoscope. The enclosure can be configured to receive a second endoscope different than the first endoscope and the electromagnetic radiation source can be configured to emit electromagnetic radiation based on a second calibration instruction associated with a second endoscope. In some embodiments, the second calibration instruction can be different than the first calibration instruction.

In some embodiments, the apparatus also can include a processor configured to trigger the endoscope to acquire at least one frame based on the electromagnetic radiation in response to the calibration instruction. In some embodiments, the electromagnetic radiation source can be a liquid crystal display.

In some embodiments, the electromagnetic radiation source can be configured to define a test pattern based on the electromagnetic radiation and the electromagnetic radiation sensor can be configured to produce a response based on the test pattern. The apparatus can also include a processor configured to modify a correction factor associated with the electromagnetic radiation sensor of the endoscope based on the response.

In some embodiments, a method can include emitting electromagnetic radiation at a first time from an electromagnetic radiation source that has at least a portion disposed within an enclosure. The method can include receiving a signal from a sensor defined based on a portion of the electromagnetic radiation received at the sensor while at least a portion of an endoscope is received within the enclosure. The method can also include emitting electromagnetic radiation at a second time different than the first time in response to the signal and based on a calibration algorithm associated with the endoscope.

In some embodiments, emitting at the first time can include emitting electromagnetic radiation defining a first calibration target and emitting at the second time can include emitting electromagnetic radiation defining a second calibration target different from the first calibration target. In some embodiments, the emitting at the first time can include emitting electromagnetic radiation defining a calibration target and emitting at the second time can include emitting electromagnetic radiation defining a test target.

In some embodiments, the sensor can be an electromagnetic radiation sensor associated with the endoscope and the method can include determining whether a responsiveness of the electromagnetic radiation sensor satisfies a failure condition based on the signal and sending a notification in response to the determining. In some embodiments, the method can include moving the electromagnetic radiation source relative to the endoscope based on the signal.

In some embodiments, the portion can be a first portion and the sensor can have a portion disposed within the enclosure. Emitting associated with the first time can include emitting such that at least a second portion of the electromagnetic radiation at the first time is received by an electromagnetic radiation sensor associated with the endoscope.

In some embodiments, the sensor can be an electromagnetic radiation sensor associated with the endoscope. The method can also include defining a correction factor associated with the electromagnetic radiation sensor based on the signal. In some embodiments, the sensor can be associated with the endoscope and the signal can be a first signal. The method can also include sending a second signal different than the first signal to the endoscope to trigger the sensor to acquire a frame associated with at least one of the electromagnetic radiation emitted at the first time or the electromagnetic radiation emitted at the second time.

In yet another embodiment, an apparatus can include an adapter that has an opening configured to receive a portion of an endoscope and a calibration unit that can be configured to receive the adapter such that an image sensor of the endoscope has a specified position relative to a target disposed within the calibration unit when the adapter is coupled to the calibration unit and the endoscope is coupled to the adapter.

In some embodiments, the target can be an active calibration component that has a portion configured to emit electromagnetic radiation based on a calibration algorithm associated with the endoscope. In some embodiments, the target can be an active test target to emit electromagnetic radiation based on a calibration algorithm associated with the endoscope.

In some embodiments, the calibration unit can have an orientation feature associated with an orientation feature of the endoscope. The image sensor can have a specified orientation within a plane normal to a longitudinal axis of the endoscope when the orientation feature of the calibration unit is aligned with the orientation feature of the endoscope.

In some embodiments, a first orientation feature associated with the adapter can be configured to mate with an orientation feature of the endoscope. A second orientation feature associated with the adapter can be configured to mate with an orientation feature associated with the calibration unit.

In some embodiments, the adapter can have a portion distal to the image sensor of the endoscope when the endoscope is coupled to the adapter. In some embodiments, the portion can be transparent to visible light. In some embodiments, a distance between the image sensor and the calibration target can be defined, at least in part, by a portion of the adapter distal to the image sensor of the endoscope when the endoscope is coupled to the adapter.

In some embodiments, the adapter can be a first adapter and the endoscope can be a first endoscope. The calibration unit can be configured receive a second adapter different than the first adapter and the second adapter can be associated with a second endoscope different than the first endoscope. In some embodiments, the apparatus can include a sensor configured to trigger execution of a calibration algorithm when the adapter is coupled to the calibration unit and the endoscope is coupled to adapter.

In some embodiments, the apparatus can include a sensor configured to send an alarm indicator when execution of a calibration algorithm is initiated and when the endoscope is not in the specified position relative to the target. In some embodiments, the calibration target can be associated with an image disposed within a plane and a longitudinal axis of the endoscope can be non-parallel to the plane when the endoscope is coupled to the adapter and the adapter is coupled to the calibration unit.

In some embodiments, the apparatus can include a processor configured to initiate execution of a calibration algorithm at a first time when the endoscope is in the specified position relative to the target and a sensor configured to terminate the execution of the calibration algorithm at a second time when the endoscope is moved from the specified position relative to the target.

Some embodiments relate to a computer storage product with a computer-readable medium (also referred to as a processor-readable medium) having instructions or computer code thereon for performing various computer-implemented operations. The media and computer code (also referred to as code) may be those specially designed and constructed for the specific purpose or purposes. Examples of computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as floptical disks; carrier wave signals; and hardware devices that are specially configured to store and execute program code, such as ASICs, Programmable Logic Devices (PLDs), and ROM and RAM devices. Examples of computer code include, but are not limited to, micro-code or micro-instructions, machine instructions, such as produced by a compiler, and files containing higher-level instructions that are executed by a computer using an interpreter. For example, an embodiment of the invention may be implemented using Java, C++, or other object-oriented programming language and development tools. Additional examples of computer code include, but are not limited to, control signals, encrypted code, and compressed code.

In conclusion, methods and apparatus for calibration of a sensor associated with an endoscope are described. Variations and substitutions may be made to achieve substantially the same results as achieved by the embodiments described herein. Accordingly, there is no intention to be limited to the disclosed exemplary forms. Many variations, modifications and alternative constructions are possible.

What is claimed is:

1. A method of calibrating an endoscope, the method comprising:
receiving a first signal indicative of a type of electromagnetic radiation sensor associated with the endoscope;
selecting one or more calibration instructions based at least in part on the first signal;
defining a first calibration target, detectable by the electromagnetic radiation sensor for calibrating one or more settings of one or more components of the endoscope, based on the one or more calibration instructions;
displaying the first calibration target;
receiving a second signal from the electromagnetic radiation sensor, wherein the second signal is indicative of what portion of the first calibration target the electromagnetic radiation sensor detected;
determining one or more correction factors, configured to adjust the one or more settings of the one or more components of the endoscope, based on the second signal; and
defining a second calibration target detectable by the electromagnetic radiation sensor, wherein one or more characteristics of the second calibration target are based at least in part on the one or more calibration instructions and the second signal.

2. The method of claim 1, wherein the one or more calibration instructions include one or more time constraints, and the one or more time constraints are determined based at least in part on the second signal.

3. The method of claim 1, wherein the first calibration target and the second calibration target include electromagnetic radiation emitted from an electromagnetic radiation source.

4. The method of claim 1, wherein the first calibration target is different than the second calibration target.

5. The method of claim 1, further comprising determining whether a responsiveness of the electromagnetic radiation sensor to the first calibration target satisfies a threshold condition based on the second signal.

6. The method of claim 1, further comprising sending a third signal to the endoscope to trigger the electromagnetic radiation sensor to acquire a frame associated with at least one of the first calibration target or the second calibration target.

7. The method of claim 1, wherein the one or more components of the endoscope include a plurality of components of the endoscope, and wherein different components of the plurality of components of the endoscope are calibrated serially.

8. The method of claim 1, wherein the one or more components of the endoscope include a plurality of components of the endoscope, and wherein different components of the plurality of components of the endoscope are calibrated in parallel.

9. The method of claim 1, further comprising sending the one or more correction factors to the endoscope to adjust the one or more settings of the one or more components of the endoscope.

10. An apparatus comprising:
an enclosure configured to receive at least a portion of an endoscope;
an electromagnetic radiation source at least partially disposed within the enclosure, wherein the electromagnetic radiation source is configured to emit electromagnetic radiation based on a calibration instruction configured to calibrate one or more operational settings of the endoscope; and
a processor configured to execute instructions to perform a method, the method including:
receiving a first signal identifying an electromagnetic radiation sensor associated with the endoscope, wherein the first signal is indicative of a type of the endoscope;
selecting the calibration instruction based on the first signal;
defining a first calibration target based on the calibration instruction;
displaying the first calibration target using the electromagnetic radiation source;
receiving a second signal from the electromagnetic radiation sensor, wherein the second signal is indicative of what portion of the first calibration target the electromagnetic radiation sensor detected;
determining one or more correction factors based on the second signal; and
defining a second calibration target, wherein one or more characteristics of the second calibration target are based at least in part on the calibration instruction and the second signal.

11. The apparatus of claim 10, wherein the method performed by the processor further comprises displaying the second calibration target using the electromagnetic radiation source.

12. The apparatus of claim 10, wherein the enclosure further comprises a seal, and wherein the seal is dimensioned to receive a distal portion of the endoscope to couple the endoscope to the enclosure.

13. The apparatus of claim 10, wherein the method performed by the processor further comprises determining whether a responsiveness of the electromagnetic radiation sensor satisfies a threshold condition based at least in part on the second signal.

14. The apparatus of claim 10, wherein the method performed by the processor further comprises sending the one or more correction factors to the endoscope.

15. The apparatus of claim 10, wherein the enclosure includes a photodetector.

16. An apparatus comprising:
an enclosure configured to receive at least a portion of an endoscope;
an electromagnetic radiation source at least partially disposed within the enclosure; and
a processor configured to execute instructions to perform a method, the method including:
emitting electromagnetic radiation from the electromagnetic radiation source at a first time when the portion of the endoscope is received within the enclosure;
receiving a signal from an electromagnetic radiation sensor of the endoscope, the signal being defined based at least in part on a portion of the electromagnetic radiation emitted at the first time and received by the electromagnetic radiation sensor while the portion of the endoscope is disposed within the enclosure;
determining whether a responsiveness of the electromagnetic radiation sensor to the electromagnetic radiation satisfies a threshold condition based at least in part on the signal; and
emitting electromagnetic radiation at a second time different than the first time, wherein one or more characteristics of the electromagnetic radiation emitted at the second time are based at least in part on the responsiveness of the electromagnetic radiation sensor, the received signal, and a calibration instruction associated with the endoscope.

17. The apparatus of claim 16, wherein the enclosure further comprises a seal, and wherein the seal is dimensioned to receive a distal portion of the endoscope to couple the endoscope to the enclosure.

18. The apparatus of claim 16, wherein the method performed by the processor further comprises selecting one or more correction factors based on the responsiveness of the electromagnetic radiation sensor.

19. The apparatus of claim 18, wherein the method performed by the processor further comprises sending the one or more correction factors to the endoscope.

20. The apparatus of claim 16, wherein the enclosure includes a photodetector.

* * * * *